April 13, 1976
A. GROB
KALANCHOE PLANT
Filed Sept. 25, 1974
Plant Pat. 3,861
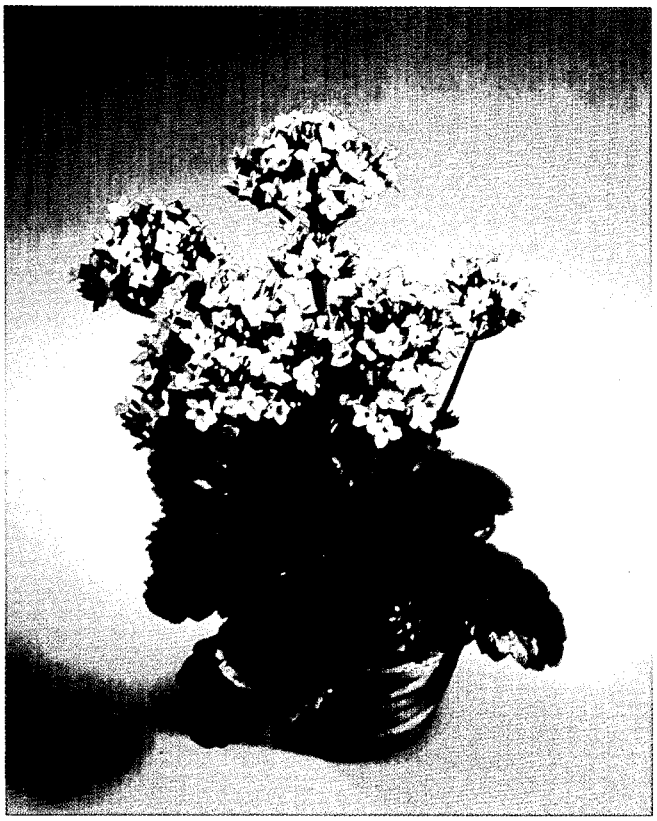

United States Patent

Plant Pat. 3,861
Patented Apr. 13, 1976

1

3,861

KALANCHOE PLANT

Adolf Grob, St. Gallen, Switzerland, assignor to Mikkelsens Inc., Ashtabula, Ohio Filed Sept. 25, 1974, Ser. No. 509,145
Int. Cl. A01h 5/00
U.S. Cl. Plt—68 1 Claim The present invention relates to a new and distinct variety of Kalanchoe plant known by the varietal name Feureball.

The new variety was discovered by me as a selected, cultivated seedling derived from a selected seedling out of Grobs Feuerwerk, the unpatented seed parent, and a second selected seedling out of Grobs Feuerwerk, the pollen parent. The new cultivar was first asexually reproduced by vegetative cuttings at St. Gallen, Switzerland, and the unique characteristics of the new cultivar have been transmitted through successive propagations.

The new cultivar is particularly characterized by being one of the most reliable Kalanchoes to force of those varieties available. It flowers for a relatively long period of time without giving the impression of having finished flowering. The new cultivar has excellent branching habits, branching readily with five to eight side breaks, and has relatively small foliage. The new cultivar is also very easy to handle as a wrapped plant in shipping containers, an important advantage from a commercial standpoint.

When compared with the cultivar Feuerzauber, disclosed in my pending application Ser. No. 509,143, filed Sept. 25, 1974, the closest variety for comparison purposes, Feuerball is more readily forced to flower under a controlled environment, has smaller foliage, flowers over a longer period of time, and is much better for handling as a wrapped plant in shipping containers.

The following description is based on plants of the new cultivar grown initially in St. Gallen, Switzerland and subsequently in Ashtabula, Ohio. Flower and foliage color values are taken from RHS Colour Chart.

The accompanying color photographic drawing shows a typical blooming plant of the new cultivar, with the color being as true as possible with color illustrations of this type.

Parentage: The new cultivar is a seedling resulting from selected, separate seedlings out of Grobs Feuerwerk, an unpatented cultivar.

Propagation: By asexually propagating by cuttings, it has been successfully demonstrated that the new cultivar is stable and produces true to type.

Form: Bush form; numerous branches; upright and compact.

Growth habit: Medium vigor; compact and branching.

Rooting: The roots of the new cultivar are fine and well branched.

Blooming habit: Reacts well to short day treatment; by means of controlled greenhouse culture, the cultivar can be flowered during the entire year; flowers consistently in 12-14 weeks after start of flowering initiation.

2

Blooming season: Natural blooming season is January–February.

Foliage: Leaves are opposite, borne at slight angle to the stem; internodal distance is very close, being 4–5 mm. between pairs of leaves.

*Size.*—5–6 cm. wide by 7–8 cm. long.

*Shape.*—Oval, with twisting the full length of leaf.

*Texture.*—Smooth, glabrous, not as thick or fleshy as Feuerzauber; crisp, coriaceous.

*Margin.*—Nearly double crenate, tendency toward purple coloration.

*Color.*—Upperside, darker than 147A, toward 139A; underside, 137B.

Disease resistance: All testing to date indicates strong resistance to common mildew. No other epidemic diseases have been seen or reported on this cultivar.

Flowers:

*Borne.*—On compound terminal spherical cymes—presenting a ball effect. Strong self-branching characteristic below the apex allows for development of an unusually high number of flower stems, upwards to 12 or 15. Main flowering stems are strong, durable, measuring between 7–10 cm. below the inflorescence. Individual flower pedicels are short. Total flowering display is unique in Kalanchoes.

*Quantity.*—Total number is greatly above the average for the Grob Kalanchoe cultivars because of number of flowering stems and the flowers in each inflorescence.

*Buds.*—Are small, approximately 5–7 mm. just before petals emerge. Covered with four light green sepals.

*Continuity.*—Flowers continuously for several months; will revegetate and flower again under proper environmental conditions.

*Petals.*—Four, occasionally five, nearly round petals are approximately 5 mm. in diameter, total flower size is nearly 12 cm. in diameter; slightly overlapping, red near 43B except in throat which is lighter toward orange.

Reproductive organs:

*Stamens.*—Eight in two stages of development, others brown, filaments light yellow green.

*Pollen.*—Yellow—abundant.

*Styles/ovaries.*—Light yellow green, stigmas yellowish white when receptive, four carpels producing multiple viable seed.

I claim:

1. A new and distinct cultivar of Kalanchoe characterized particularly by its ability to flower continuously for several months and flower again after revegetation under proper environmental conditions; by its excellent branching habit and relatively small foliage, and its ease of handling for wrapping and shipping.

No references cited.

ROBERT E. BAGWILL, Primary Examiner